(12) United States Patent
Old

(10) Patent No.: US 7,553,860 B2
(45) Date of Patent: Jun. 30, 2009

(54) SUBSTITUTED GAMMA LACTAMS AS THERAPEUTIC AGENTS

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 74 days.

(21) Appl. No.: 11/758,792

(22) Filed: Jun. 6, 2007

(65) Prior Publication Data

US 2007/0293551 A1 Dec. 20, 2007

Related U.S. Application Data

(60) Provisional application No. 60/804,680, filed on Jun. 14, 2006.

(51) Int. Cl.
*A61K 31/421* (2006.01)
*C07D 263/04* (2006.01)
(52) U.S. Cl. .................................. 514/376; 548/229
(58) Field of Classification Search ............. 514/369, 514/424, 376, 395; 548/182, 229, 316.4, 548/542, 183, 186, 188, 200, 226, 230, 232, 548/318.5, 319.1, 321.1, 322.5
See application file for complete search history.

(56) References Cited

U.S. PATENT DOCUMENTS

| 5,902,726 A | 5/1999 | Kliewer et al. |
| 6,573,294 B1 | 6/2003 | Old et al. |

FOREIGN PATENT DOCUMENTS

| WO | WO 2006/098918 | 9/2006 |

OTHER PUBLICATIONS

Wolff et al., Burger's Medicinal Chemistry and Drug Discovery, 1994, Wiley-Interscience, Fifth Edition, vol. I: Principles and Practice, pp. 975-977.*
Metabolomics [online], Retrieved from the Internet Jun. 16, 2008, www.en.wikipedia.org/wiki/Metabolomics.*
Kwon et al., Handbook of Essential Pharmacokinetics, Pharmacodynamics and Drug Metabolism for Industrial Scientists, 2001, http://www.myilibrary.com/Browse/open.asp?ID=4284 &loc=1, Retrieved from the Internet Jun. 16, 2008, p. 213.*
Ding et al., An efficient synthesis of optically pure (S)-2-functionalized 1,2,3,4-tetrahydroquinoline, 2004, Tetrahedron Letters, 45, 1027-1029.*
Baxter, Anthony D., et al., "Synthesis and Use of 7-Substituted Norbornadienes + for the Preparation of Prostaglandins and Prostanoids," J. Chem. Soc. Perkin Trans. I, 1986, pp. 889-900.
Dragoli, Dean R., et al., "Parallel Synthesis of Prostaglandin E₁ Analogues," J. Comb. Chem. 19999, I, pp. 534-539.

* cited by examiner

*Primary Examiner*—Kamal A Saeed
*Assistant Examiner*—Kristin Bianchi
(74) *Attorney, Agent, or Firm*—Allergan, Inc.; Kevin Forrestal

(57) ABSTRACT

A compound having the formula

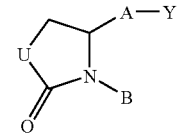

or a pharmaceutically acceptable salt or a prodrug thereof is disclosed herein. Y, A, and B are as described herein.

Methods, compositions, and medicaments related to these compounds are also disclosed.

20 Claims, No Drawings

SUBSTITUTED GAMMA LACTAMS AS THERAPEUTIC AGENTS

RELATED APPLICATION

This application is based, and claims priority under 35 U.S.C. § 120 to U.S. Provisional Application Ser. No. 60/804,680, filed Jun. 14, 2006, which is hereby incorporated by reference in its entirety.

DESCRIPTION OF THE INVENTION

Compounds are disclosed herein having the formula

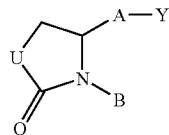

or a pharmaceutically acceptable salt or a prodrug thereof;

wherein Y is an organic acid functional group, or an amide or ester thereof comprising up to 12 carbon atoms; or Y is hydroxymethyl or an ether thereof comprising up to 12 carbon atoms; or Y is a tetrazolyl functional group;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

U is O, S, $NR^1$, wherein $R^1$ is H, $C_{1-6}$alkyl, $C_{1-7}$acyl, benzoyl, biphenylacyl, $C_{1-6}$sulfonyl, phenylsulfonyl, biphenylsulfonyl, trifluoromethylacyl, or trifloyl; and B is aryl or heteroaryl.

Y is an organic acid functional group, or an amide or ester thereof comprising up to 12 carbon atoms; or Y is hydroxymethyl or an ether thereof comprising up to 12 carbon atoms; or Y is a tetrazolyl functional group.

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group, i.e. one of the structures shown below.

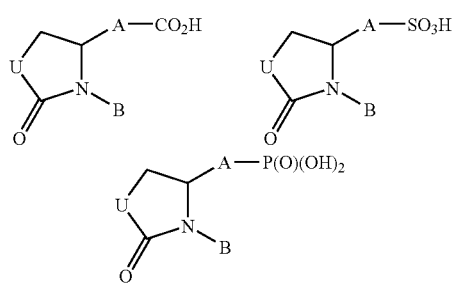

Salts of any of these acids of any pharmaceutically acceptable form are also contemplated.

Additionally, an amide or ester of one of the organic acids shown above comprising up to 12 carbon atoms is also contemplated. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$.

While not intending to limit the scope of the invention in any way, Y may also be hydroxymethyl or an ether thereof comprising up to 12 carbon atoms. Thus, compounds having a structure shown below are possible.

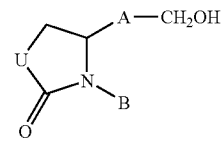

Additionally, ethers of these compounds are also possible. An ether is a functional group wherein a hydrogen of an hydroxyl is replaced by carbon, e.g., Y is $CH_2OCH_3$, $CH_2OCH_2CH_3$, etc.

Finally, while not intending to limit the scope of the invention in any way, Y may be a tetrazolyl functional group, such as compounds having a structure according to the formula below.

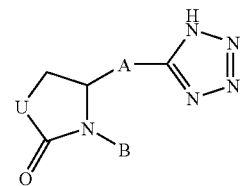

An unsubstituted tetrazolyl functional group has two tautomeric forms, which can rapidly interconvert in aqueous or biological media, and are thus equivalent to one another. These tautomers are shown below.

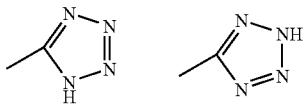

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

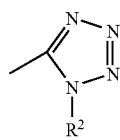

While not intending to limit the scope of the invention in any way, in one embodiment, Y is selected from the group consisting of $CO_2(R^2)$, $CON(R^2)_2$, $CON(OR^2)R^2$, $CON(CH_2CH_2OH)_2$, $CONH(CH_2CH_2OH)$, $CH_2OH$, $P(O)(OH)_2$, CONHSO$_2$R$^2$, SO$_2$N(R$^2$)$_2$, SO$_2$NHR$^2$, and tetrazolyl-R$^2$; wherein R$^2$ is independently H, C$_1$-C$_6$ alkyl, phenyl, or biphenyl.

In another embodiment Y is not CONH-phenyl or CONH-cyclohexyl.

In relation to the identity of A disclosed in the chemical structures presented herein, A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O.

While not intending to be limiting, A may be —(CH$_2$)$_6$—, cis —CH$_2$CH=CH—(CH$_2$)$_3$—, or —CH$_2$C≡C—(CH$_2$)$_3$—.

Alternatively, A may be a group which is related to one of these three moieties in that any carbon is substituted with S and/or O. For example, while not intending to limit the scope of the invention in any way, A may be an S substituted moiety such as one of the following or the like.

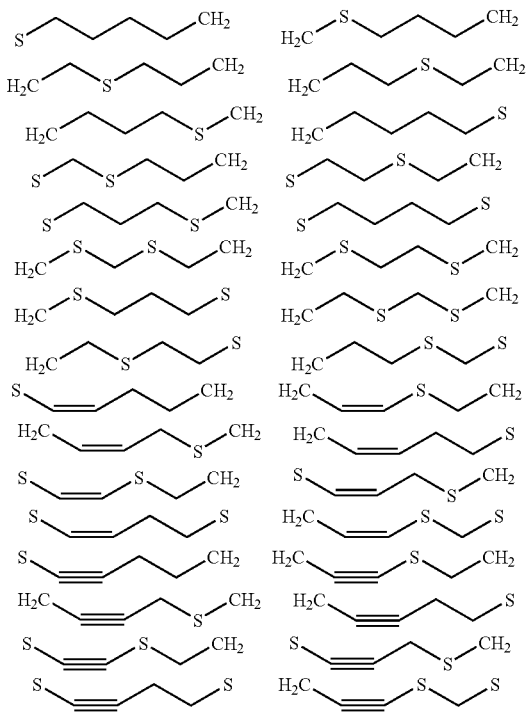

Alternatively, while not intending to limit the scope of the invention in any way, A may be an O substituted moiety such as one of the following or the like.

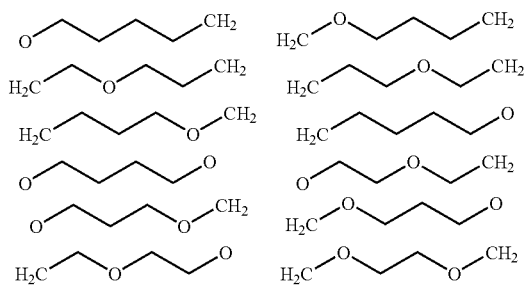

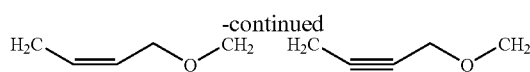

Alternatively, while not intending to limit the scope of the invention in any way, A may have both an O and an S substituted into the chain, such as one of the following or the like.

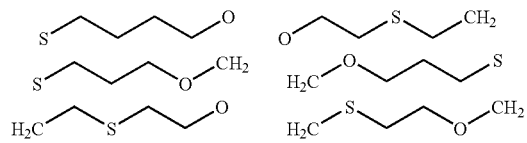

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O. In other words, while not intending to limit the scope of the invention in any way, in one embodiment A comprises from 1 to 4 CH$_2$ moieties and Ar, e.g. —CH$_2$—Ar—, —(CH$_2$)$_2$—Ar—, —CH$_2$—Ar—CH$_2$—, —CH$_2$—Ar—(CH$_2$)$_2$—, —(CH$_2$)$_2$—Ar—(CH$_2$)$_2$—, and the like; or A comprises O, from 0 to 3 CH$_2$ moieties, and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or A comprises S, from 0 to 3 CH$_2$ moieties, and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —(CH$_2$)$_2$—S—Ar, and the like.

In another embodiment, the sum of m and o is from 2 to 4 wherein one CH$_2$ may be substituted with S or O.

In another embodiment, the sum of m and o is 3 wherein one CH$_2$ may be substituted with S or O.

In another embodiment, the sum of m and o is 2 wherein one CH$_2$ may be substituted with S or O.

In another embodiment, the sum of m and o is 4 wherein one CH$_2$ may be substituted with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has one or more substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$—Ph-. While not intending to limit scope of the invention in any way, substituents may have 4 or less heavy atoms, or in other words, non hydrogen atoms. Any number of hydrogen atoms required for a particular substituent will also be included. Thus, the substituent may be hydrocarbyl, i.e. a moiety consisting of only carbon and hydrogen such as alkyl, having up to 4 carbon atoms, including alkyl up to C$_4$, alkenyl, alkynyl, and the like; hydrocarbyloxy up to C$_3$;

CF$_3$;

halo, such as F, Cl, or Br;

hydroxyl;

NH$_2$ and alkylamine functional groups up to C$_3$;
other N or S containing substituents;
and the like.

Substituted interarylene or interheteroarylene may have one or more substituents, up to as many as the ring or ring system will bear, and the substituents may be the same or different. Thus, for example, an interarylene ring or interheteroarylene ring may be substituted with chloro and methyl; methyl, OH, and F; CN, NO$_2$, and ethyl; and the like including any conceivable substituent or combination of substituent possible in light of this disclosure.

In one embodiment A is —(CH$_2$)$_m$—Ar—(CH$_2$)$_o$— wherein Ar is interphenylene, the sum of m and o is from 1 to 3, and wherein one CH$_2$ may be substituted with S or O.

In another embodiment A is —CH$_2$—Ar—OCH$_2$—. In another embodiment A is —CH$_2$—Ar—OCH$_2$— and Ar is interphenylene. In another embodiment, Ar is 1,3 interaryl or interheteroaryl, where Ar attached at the 1 and 3 positions, such as when A has the structure shown below.

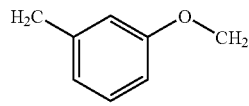

Other examples of 1,3 interaryl or interheteroaryl are exemplified in the following examples of A-Y.

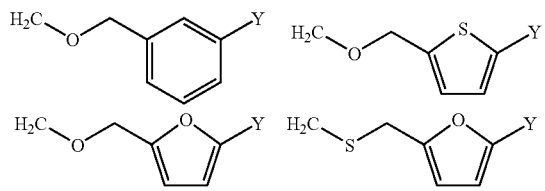

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_2$—Ph- wherein one CH$_2$ may be substituted with S or O.

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_2$—Ph-.

In another embodiment A is not —(CH$_2$)$_6$—.

In other embodiments, A has one of the following structures, where Y is attached to the oxazolyl or thiazolyl ring.

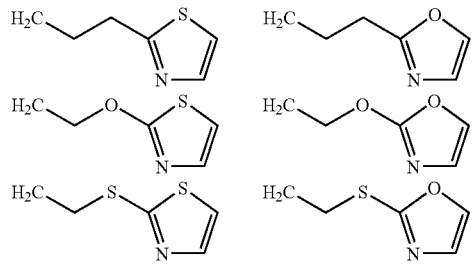

In other embodiments A is one of the structures shown below, where Y is attached to the phenyl or heteroaryl ring.

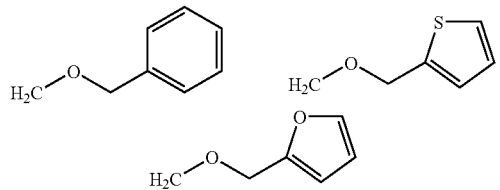

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH═CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene.
In another embodiment A is —CH$_2$—O—(CH$_2$)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.

U is O, S, NR$^1$, wherein R$^1$ is H, C$_{1-6}$ alkyl, C$_{1-7}$ acyl, benzoyl, biphenylacyl, C$_{1-6}$ sulfonyl, phenylsulfonyl, biphenylsulfonyl, trifluoromethylacyl, or trifloyl.

Acyl, benzoyl, biphenylacyl, sulfonyl, phenylsulfonyl, and biphenylsulfonyl have the structures shown below, where N indicates the nitrogen atom of U.

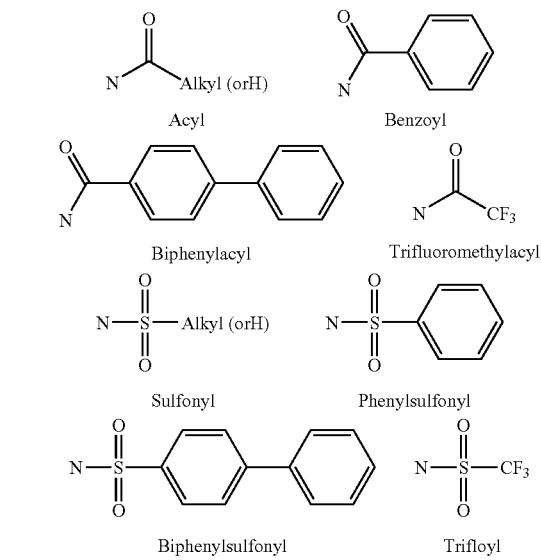

Thus, compounds according to the formulas shown below are possible, or pharmaceutically acceptable salts or prodrugs thereof, wherein R$^7$ is H or C$_{1-6}$ alkyl.

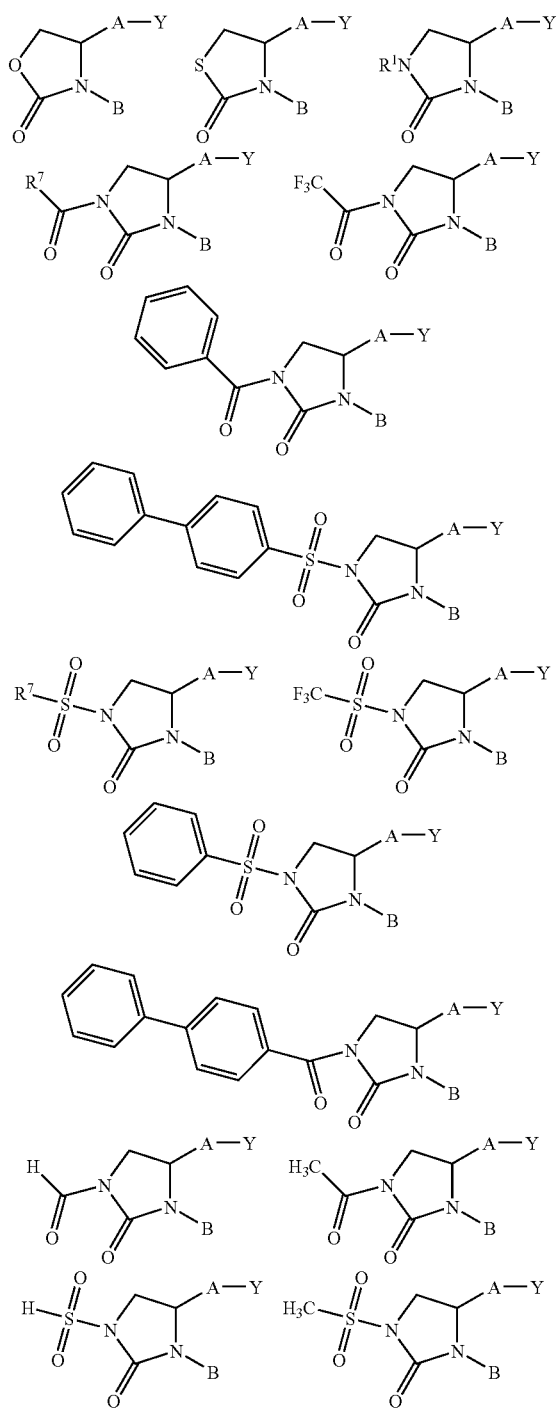

In one embodiment, $R^7$ is H. In another embodiment $R^7$ is methyl. In another embodiment $R^7$ is ethyl. In another embodiment $R^7$ a propyl isomer. In another embodiment $R^7$ is H or $C_{1-3}$ alkyl.

B is aryl or heteroaryl.

Aryl is an unsubstituted or substituted aromatic ring or ring system such as phenyl, naphthyl, biphenyl, and the like.

Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

The substituents of aryl or heteroaryl may have up to 12 non-hydrogen atoms each and as many hydrogen atoms as necessary. Thus, while not intending to limit the scope of the invention in any way, the substituents may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as $OCH_3$, $OCH_2CH_3$, O-cyclohexyl, etc, up to 11 carbon atoms;

other ether substituents such as $CH_2OCH_3$, $(CH_2)_2OCH(CH_3)_2$, and the like;

thioether substituents including S-hydrocarbyl and other thioether substituents;

hydroxyhydrocarbyl, meaning hydrocarbyl-OH such as $CH_2OH$, $C(CH_3)_2OH$, etc, up to 11 carbon atoms;

nitrogen substituents such as $NO_2$, CN, and the like, including amino, such as $NH_2$, $NH(CH_2CH_3OH)$, $NHCH_3$, and the like up to 11 carbon atoms;

carbonyl substituents, such as $CO_2H$, ester, amide, and the like;

halogen, such as chloro, fluoro, bromo, and the like fluorocarbyl, such as $CF_3$, $CF_2CF_3$, etc.;

phosphorous substituents, such as $PO_3^{2-}$, and the like;

sulfur substituents, including S-hydrocarbyl, SH, $SO_3H$, $SO_2$-hydrocarbyl, $SO_3$-hydrocarbyl, and the like.

In certain embodiments, the number of non-hydrogen atoms is 6 or less in a substituent. In other embodiments, the number of non-hydrogen atoms is 3 or less in a substituent. In other embodiments, the number of non-hydrogen atoms on a substituent is 1.

In certain embodiments, the substituents contain only hydrogen, carbon, oxygen, halogen, nitrogen, and sulfur. In other embodiments, the substituents contain only hydrogen, carbon, oxygen, and halogen.

Unless otherwise indicated, references to aryl, heteroaryl, phenyl, thienyl, benzothienyl, and the like are intended to mean both the substituted and the unsubstituted moiety.

Substituted aryl or heteroaryl may have one or more substituents, up to as many as the ring or ring system will bear, and the substituents may be the same or different. Thus, for example, an aryl ring or a heteroaryl ring may be substituted with chloro and methyl; methyl, OH, and F; CN, $NO_2$, and ethyl; and the like including any conceivable substituent or combination of substituent possible in light of this disclosure.

Thus, compounds wherein B is any of the above classes or species of aryl or heteroaryl are contemplated herein.

Further, while not intending to limit the scope of the invention in any way, in one embodiment B is phenyl. In another embodiment B is chlorophenyl, meaning phenyl with one or more chloro substituents. In another embodiment D is 3,5-dichlorophenyl. In another embodiment B is unsubstituted phenyl. In another embodiment B is alkylphenyl. In another embodiment B is t-butylphenyl.

In another embodiment B is hydroxyalkylphenyl, meaning phenyl with a hydroxyalkyl substituent such as Ph-CH(OH)$C(CH_3)_3$.

B can also be any of the groups shown below, where the remainder of the molecule attaches to the phenyl ring. The names of these moieties are shown to the right of the structure.

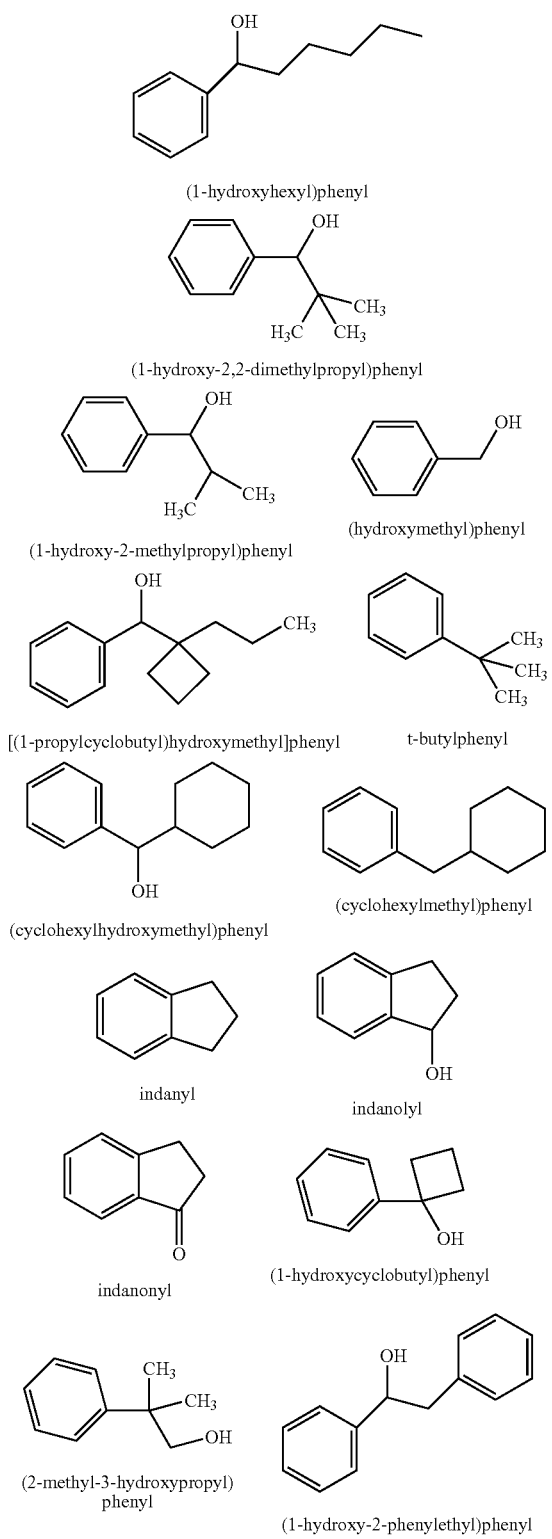

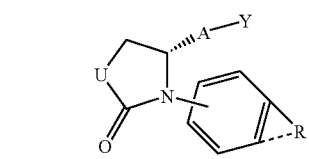

In one embodiment, x is 5 and y+z is 11.
In another embodiment, x is 6 and y+z is 13.
In another embodiment, x is 7 and y+z is 15.
Compounds have the formula

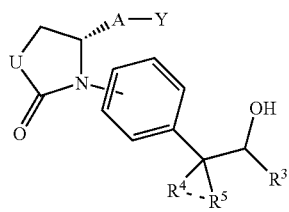

or a pharmaceutically acceptable salt or a prodrug thereof;

wherein a dashed line indicates the presence or absence of a bond
R is hydrocarbyl or hydroxyhydrocarbyl having from 1 to 12 carbon atoms.
Other compounds have the formula

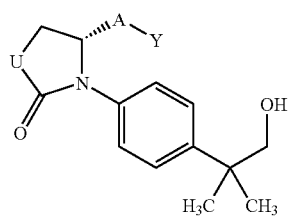

or a pharmaceutically acceptable salt or a prodrug thereof;

wherein a dashed line indicates the presence or absence of a bond;
$R^3$, $R^4$, and $R^5$ are independently H or $C_{1-6}$ alkyl.

As the dashed line indicates the presence or absence of a bond, $R^4$ and $R^5$ may be two separate moieties. For example, while not intending to be limiting, in one embodiment $R^4$ and $R^5$ is methyl, and no bond is present where indicated by the dashed line.

For example, a compound according to the formula below or a pharmaceutically acceptable salt or a prodrug thereof is contemplated. Alternatively, while not intending to limit the In other embodiments, B has one of the structures below, where the remainder of the molecule attaches to the phenyl ring, and wherein x is 5, 6, or 7, and y+z is 2x+1.

scope of the invention in any way, $R^4$ and $R^5$ may form a ring. In other words, a compound such as the one shown below is possible, wherein x is from 1 to 6.

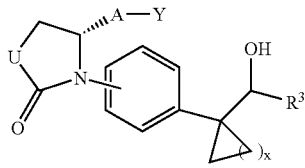

A pharmaceutically acceptable salt, prodrug, or a metabolite thereof is also contemplated.

Another embodiment has the formula

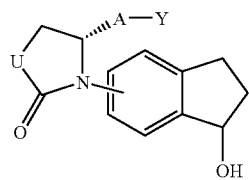

A pharmaceutically acceptable salt, prodrug, or a metabolite thereof is also contemplated.

Other useful compounds have the formula

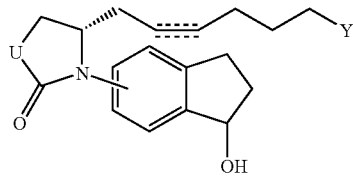

A pharmaceutically acceptable salt, prodrug, or a metabolite thereof is also contemplated.

Other useful examples of compounds have the formula

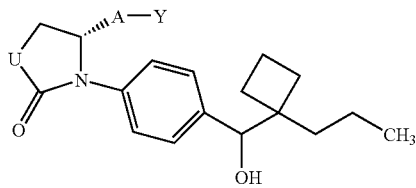

or a pharmaceutically acceptable salt or a prodrug thereof.

Other compounds have the formula

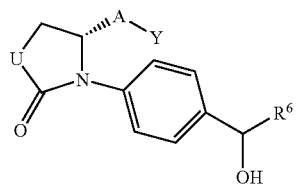

or a pharmaceutically acceptable salt or a prodrug thereof, wherein $R^6$ is cycloalkyl comprising from 3 to 10 carbon atoms.

Other compounds have the formula

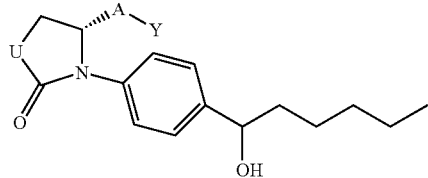

or a pharmaceutically acceptable salt or a prodrug thereof.

Other compounds have the formula

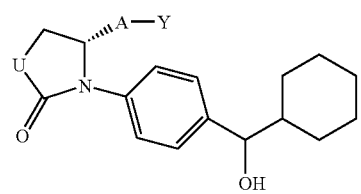

or a pharmaceutically acceptable salt or a prodrug thereof.

Other compounds have the formula

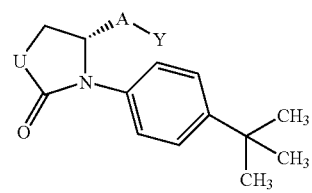

or a pharmaceutically acceptable salt, prodrug, or a metabolite thereof.

Another useful compound is

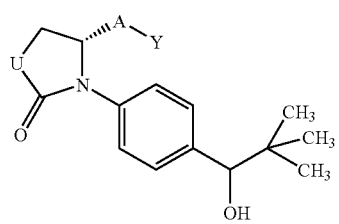

or a pharmaceutically acceptable salt or a prodrug thereof.

Another useful compound is

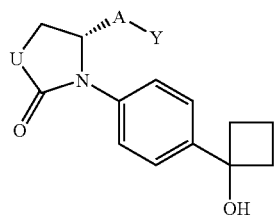

or a pharmaceutically acceptable salt or a prodrug thereof.

E is unsubstituted phenyl, chlorophenyl, fluorophenyl, or dimethylaminophenyl.

Other compounds have the formula

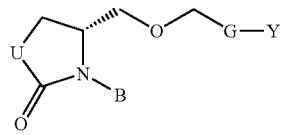

or a pharmaceutically acceptable salt or a prodrug thereof; wherein G is 1,3-interaryl or interheteroaryl, or —(CH$_2$)$_3$—.

Other compounds have the formula

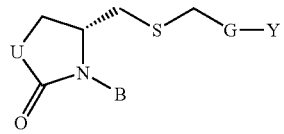

or a pharmaceutically acceptable salt or a prodrug thereof; wherein G is 1,3-interaryl or interheteroaryl, or —(CH$_2$)$_3$—.

Other compounds have the formula

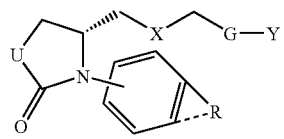

or a pharmaceutically acceptable salt or a prodrug thereof;

wherein a dashed line indicates the presence or absence of a bond;

R is hydrocarbyl or hydroxyhydrocarbyl having from 1 to 12 carbon atoms;

X is CH$_2$, O, or S; and

G is 1,3-interaryl or interheteroaryl, or —(CH$_2$)$_3$—.

While not intending to limit the scope of the invention in any way, examples of useful compounds are depicted below, and pharmaceutically acceptable salts or prodrugs thereof.

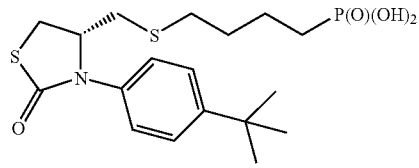

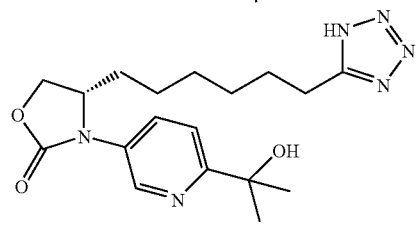

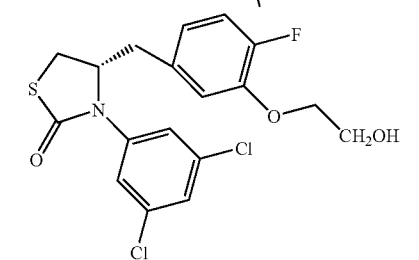

-continued

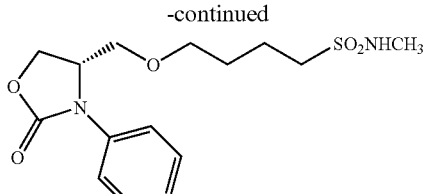

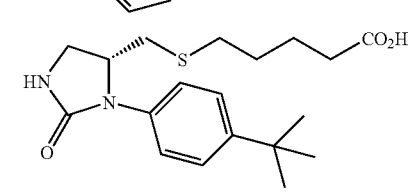

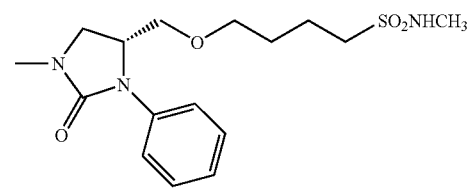

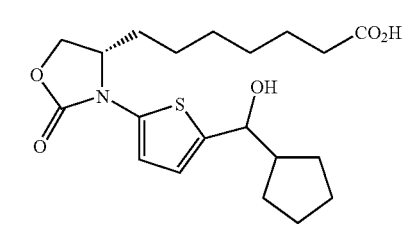

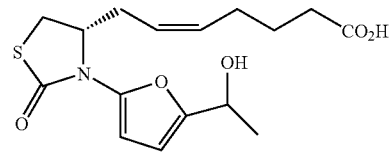

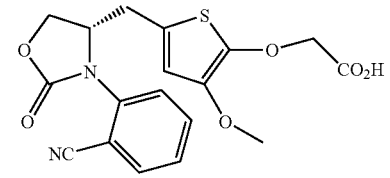

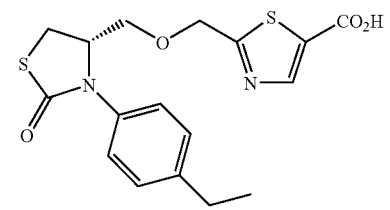

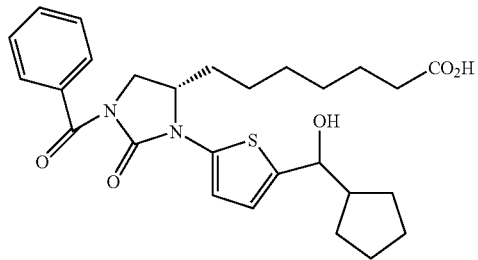

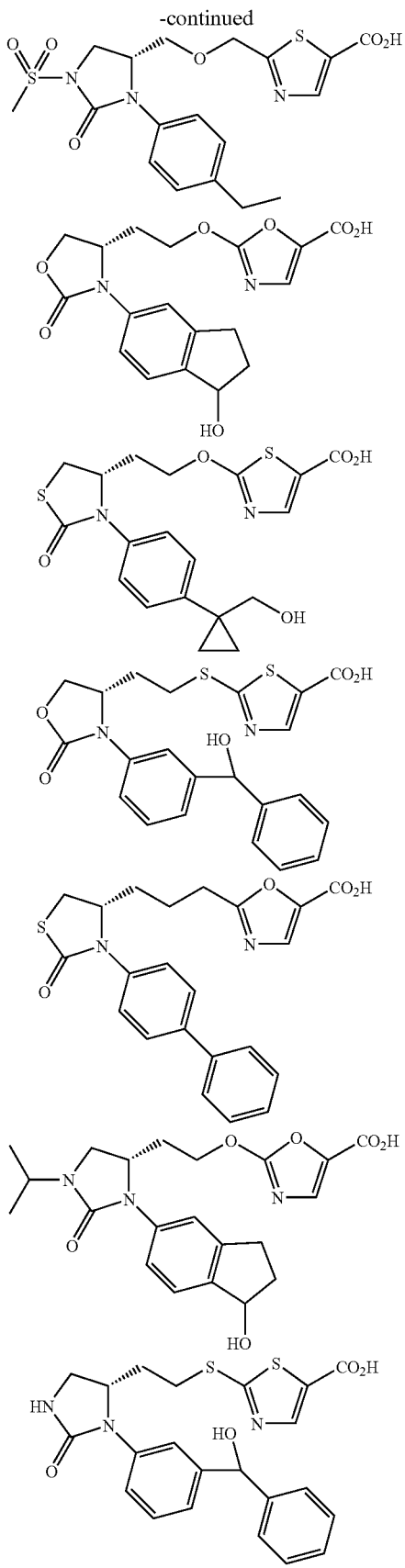

In one embodiment A is —S(CH$_2$)$_3$S(CH$_2$)$_2$— and B is phenyl.

In another embodiment A is —(CH$_2$)$_4$OCH$_2$— and B is phenyl.

In another embodiment A is cis —CH$_2$CH=CH—CH$_2$OCH$_2$— and B is phenyl.

In another embodiment A is —CH$_2$CH≡CH—CH$_2$OCH$_2$— and B is phenyl.

In another embodiment A is —(CH$_2$)$_2$S(CH$_2$)$_3$— and B is phenyl.

In another embodiment A is —CH$_2$-Ph-OCH$_2$—, wherein Ph is interphenylene, and B is phenyl.

In another embodiment A is —CH$_2$-mPh-OCH$_2$—, wherein mPh is m-interphenylene, and B is phenyl.

In another embodiment A is —CH$_2$—O—(CH$_2$)$_4$— and B is phenyl.

In another embodiment A is —CH$_2$—O—CH$_2$—Ar—, wherein Ar is 2,5-interthienylene, and B is phenyl.

In another embodiment A is —CH$_2$—O—CH$_2$—Ar—, wherein Ar is 2,5-interfurylene, and B is phenyl.

As mentioned before, phenyl in the above embodiments means substituted or unsubstituted phenyl unless indicated otherwise.

In one embodiment A is —S(CH$_2$)$_3$S(CH$_2$)$_2$— and B is (1-hydroxyhexyl)phenyl.

In another embodiment A is —(CH$_2$)$_4$OCH$_2$— and B is (1-hydroxyhexyl)phenyl.

In another embodiment A is cis —CH$_2$CH=CH—CH$_2$OCH$_2$— and B is (1-hydroxyhexyl)phenyl.

In another embodiment A is —CH$_2$CH≡CH—CH$_2$OCH$_2$— and B is (1-hydroxyhexyl)phenyl.

In another embodiment A is —(CH$_2$)$_2$S(CH$_2$)$_3$— and B is (1-hydroxyhexyl)phenyl.

In another embodiment A is —CH$_2$-Ph-OCH$_2$—, wherein Ph is interphenylene, and B is (1-hydroxyhexyl)phenyl.

In another embodiment A is —CH$_2$-mPh-OCH$_2$—, wherein mPh is m-interphenylene, and B is (1-hydroxyhexyl)phenyl.

In another embodiment A is —CH$_2$—O—(CH$_2$)$_4$— and B is (1-hydroxyhexyl)phenyl.

In another embodiment A is —CH$_2$—O—CH$_2$—Ar—, wherein Ar is 2,5-interthienylene, and B is (1-hydroxyhexyl)phenyl.

In another embodiment A is —CH$_2$—O—CH$_2$—Ar—, wherein Ar is 2,5-interfurylene, and B is (1-hydroxyhexyl)phenyl.

In another embodiment A is —S(CH$_2$)$_3$S(CH$_2$)$_2$— and B is (1-hydroxy-2,2-dimethylpropyl)phenyl.

In another embodiment A is —(CH$_2$)$_4$OCH$_2$— and B is (1-hydroxy-2,2-dimethylpropyl)phenyl.

In another embodiment A is cis —CH$_2$CH=CH—CH$_2$OCH$_2$— and B is (1-hydroxy-2,2-dimethylpropyl)phenyl.

In another embodiment A is —CH$_2$CH≡CH—CH$_2$OCH$_2$— and B is (1-hydroxy-2,2-dimethylpropyl)phenyl.

In another embodiment A is —(CH$_2$)$_2$S(CH$_2$)$_3$— and B is (1-hydroxy-2,2-dimethylpropyl)phenyl.

In another embodiment A is —CH$_2$-Ph-OCH$_2$—, wherein Ph is interphenylene, and B is (1-hydroxy-2,2-dimethylpropyl)phenyl.

In another embodiment A is —CH$_2$-mPh-OCH$_2$—, wherein mPh is m-interphenylene, and B is (1-hydroxy-2,2-dimethylpropyl)phenyl.

In another embodiment A is —CH$_2$—O—(CH$_2$)$_4$— and B is (1-hydroxy-2,2-dimethylpropyl)phenyl.

In another embodiment A is —CH$_2$—O—CH$_2$—Ar—, wherein Ar is 2,5-interthienylene, and B is (1-hydroxy-2,2-dimethylpropyl)phenyl.

In another embodiment A is —CH$_2$—O—CH$_2$—Ar—, wherein Ar is 2,5-interfurylene, and B is (1-hydroxy-2,2-dimethylpropyl)phenyl.

In another embodiment A is —S(CH$_2$)$_3$S(CH$_2$)$_2$— and B is (1-hydroxy-2-methylpropyl)phenyl.

In another embodiment A is —(CH$_2$)$_4$OCH$_2$— and B is (1-hydroxy-2-methylpropyl)phenyl.

In another embodiment A is cis —CH$_2$CH=CH—CH$_2$OCH$_2$— and B is (1-hydroxy-2-methylpropyl)phenyl.

In another embodiment A is —CH$_2$CH≡CH—CH$_2$OCH$_2$— and B is (1-hydroxy-2-methylpropyl)phenyl.

In another embodiment A is —(CH$_2$)$_2$S(CH$_2$)$_3$— and B is (1-hydroxy-2-methylpropyl)phenyl.

In another embodiment A is —CH$_2$-Ph-OCH$_2$—, wherein Ph is interphenylene, and B is (1-hydroxy-2-methylpropyl)phenyl.

In another embodiment A is —CH$_2$-mPh-OCH$_2$—, wherein mPh is m-interphenylene, and B is (1-hydroxy-2-methylpropyl)phenyl.

In another embodiment A is —CH$_2$—O—(CH$_2$)$_4$— and B is (1-hydroxy-2-methylpropyl)phenyl.

In another embodiment A is —CH$_2$—O—CH$_2$—Ar—, wherein Ar is 2,5-interthienylene, and B is (1-hydroxy-2-methylpropyl)phenyl.

In another embodiment A is —CH$_2$—O—CH$_2$—Ar—, wherein Ar is 2,5-interfurylene, and B is (1-hydroxy-2-methylpropyl)phenyl.

In another embodiment A is —S(CH$_2$)$_3$S(CH$_2$)$_2$— and B is (hydroxymethyl)phenyl.

In another embodiment A is —(CH$_2$)$_4$OCH$_2$— and B is (hydroxymethyl)phenyl.

In another embodiment A is cis —CH$_2$CH=CH—CH$_2$OCH$_2$— and B is (hydroxymethyl)phenyl.

In another embodiment A is —CH$_2$CH≡CH—CH$_2$OCH$_2$— and B is (hydroxymethyl)phenyl.

In another embodiment A is —(CH$_2$)$_2$S(CH$_2$)$_3$— and B is (hydroxymethyl)phenyl.

In another embodiment A is —CH$_2$-Ph-OCH$_2$—, wherein Ph is interphenylene, and B is (hydroxymethyl)phenyl.

In another embodiment A is —CH$_2$-mPh-OCH$_2$—, wherein mPh is m-interphenylene, and B is (hydroxymethyl)phenyl.

In another embodiment A is —CH$_2$—O—(CH$_2$)$_4$— and B is (hydroxymethyl)phenyl.

In another embodiment A is —CH$_2$—O—CH$_2$—Ar—, wherein Ar is 2,5-interthienylene, and B is (hydroxymethyl)phenyl.

In another embodiment A is —CH$_2$—O—CH$_2$—Ar—, wherein Ar is 2,5-interfurylene, and B is (hydroxymethyl)phenyl.

In another embodiment A is —S(CH$_2$)$_3$S(CH$_2$)$_2$— and B is [(1-propylcyclobutyl)hydroxymethyl]phenyl.

In another embodiment A is —(CH$_2$)$_4$OCH$_2$— and B is [(1-propylcyclobutyl)hydroxymethyl]phenyl.

In another embodiment A is cis —CH$_2$CH=CH—CH$_2$OCH$_2$— and B is [(1-propylcyclobutyl)hydroxymethyl]phenyl.

In another embodiment A is —CH$_2$CH≡CH—CH$_2$OCH$_2$— and B is [(1-propylcyclobutyl)hydroxymethyl]phenyl.

In another embodiment A is —(CH$_2$)$_2$S(CH$_2$)$_3$— and B is [(1-propylcyclobutyl)hydroxymethyl]phenyl.

In another embodiment A is —CH$_2$-Ph-OCH$_2$—, wherein Ph is interphenylene, and B is [(1-propylcyclobutyl)hydroxymethyl]phenyl.

In another embodiment A is —CH$_2$-mPh-OCH$_2$—, wherein mPh is m-interphenylene, and B is [(1-propylcyclobutyl)hydroxymethyl]phenyl.

In another embodiment A is —CH$_2$—O—(CH$_2$)$_4$— and B is [(1-propylcyclobutyl)hydroxymethyl]phenyl.

In another embodiment A is —CH$_2$—O—CH$_2$—Ar—, wherein Ar is 2,5-interthienylene, and B is [(1-propylcyclobutyl)hydroxymethyl]phenyl.

In another embodiment A is —CH$_2$—O—CH$_2$—Ar—, wherein Ar is 2,5-interfurylene, and B is [(1-propylcyclobutyl)hydroxymethyl]phenyl.

In another embodiment A is —S(CH$_2$)$_3$S(CH$_2$)$_2$— and B is t-butylphenyl.

In another embodiment A is —(CH$_2$)$_4$OCH$_2$— and B is t-butylphenyl.

In another embodiment A is cis —CH$_2$CH=CH—CH$_2$OCH$_2$— and B is t-butylphenyl.

In another embodiment A is —CH$_2$CH≡CH—CH$_2$OCH$_2$— and B is t-butylphenyl.

In another embodiment A is —(CH$_2$)$_2$S(CH$_2$)$_3$— and B is t-butylphenyl.

In another embodiment A is —CH$_2$-Ph-OCH$_2$—, wherein Ph is interphenylene, and B is t-butylphenyl.

In another embodiment A is —CH$_2$-mPh-OCH$_2$—, wherein mPh is m-interphenylene, and B is t-butylphenyl.

In another embodiment A is —CH$_2$—O—(CH$_2$)$_4$— and B is t-butylphenyl.

In another embodiment A is —CH$_2$—O—CH$_2$—Ar—, wherein Ar is 2,5-interthienylene, and B is t-butylphenyl.

In another embodiment A is —CH$_2$—O—CH$_2$—Ar—, wherein Ar is 2,5-interfurylene, and B is t-butylphenyl.

In another embodiment A is —S(CH$_2$)$_3$S(CH$_2$)$_2$— and B is (cyclohexylhydroxymethyl)phenyl.

In another embodiment A is —(CH$_2$)$_4$OCH$_2$— and B is (cyclohexylhydroxymethyl)phenyl.

In another embodiment A is cis —CH$_2$CH=CH—CH$_2$OCH$_2$— and B is (cyclohexylhydroxymethyl)phenyl.

In another embodiment A is —CH$_2$CH≡CH—CH$_2$OCH$_2$— and B is (cyclohexylhydroxymethyl)phenyl.

In another embodiment A is —(CH$_2$)$_2$S(CH$_2$)$_3$— and B is (cyclohexylhydroxymethyl)phenyl.

In another embodiment A is —CH$_2$-Ph-OCH$_2$—, wherein Ph is interphenylene, and B is (cyclohexylhydroxymethyl)phenyl.

In another embodiment A is —CH$_2$-mPh-OCH$_2$—, wherein mPh is m-interphenylene, and B is (cyclohexylhydroxymethyl)phenyl.

In another embodiment A is —CH$_2$—O—(CH$_2$)$_4$— and B is (cyclohexylhydroxymethyl)phenyl.

In another embodiment A is —CH$_2$—O—CH$_2$—Ar—, wherein Ar is 2,5-interthienylene, and B is (cyclohexylhydroxymethyl)phenyl.

In another embodiment A is —CH$_2$—O—CH$_2$—Ar—, wherein Ar is 2,5-interfurylene, and B is (cyclohexylhydroxymethyl)phenyl.

In another embodiment A is —S(CH$_2$)$_3$S(CH$_2$)$_2$— and B is (cyclohexylmethyl)phenyl.

In another embodiment A is —(CH$_2$)$_4$OCH$_2$— and B is (cyclohexylmethyl)phenyl.

In another embodiment A is cis —CH$_2$CH=CH—CH$_2$OCH$_2$— and B is (cyclohexylmethyl)phenyl.

In another embodiment A is —CH$_2$CH≡CH—CH$_2$OCH$_2$— and B is (cyclohexylmethyl)phenyl.

In another embodiment A is —(CH$_2$)$_2$S(CH$_2$)$_3$— and B is (cyclohexylmethyl)phenyl.

In another embodiment A is —CH$_2$-Ph-OCH$_2$—, wherein Ph is interphenylene, and B is (cyclohexylmethyl)phenyl.

In another embodiment A is —CH$_2$-mPh-OCH$_2$—, wherein mPh is m-interphenylene, and B is (cyclohexylmethyl)phenyl.

In another embodiment A is —CH$_2$—O—(CH$_2$)$_4$— and B is (cyclohexylmethyl)phenyl.

In another embodiment A is —CH$_2$—O—CH$_2$—Ar—, wherein Ar is 2,5-interthienylene, and B is (cyclohexylmethyl)phenyl.

In another embodiment A is —CH$_2$—O—CH$_2$—Ar—, wherein Ar is 2,5-interfurylene, and B is (cyclohexylmethyl)phenyl.

In another embodiment A is —S(CH$_2$)$_3$S(CH$_2$)$_2$— and B is indanyl.

In another embodiment A is —(CH$_2$)$_4$OCH$_2$— and B is indanyl.

In another embodiment A is cis —CH$_2$CH═CH—CH$_2$OCH$_2$— and B is indanyl.

In another embodiment A is —CH$_2$CH≡CH—CH$_2$OCH$_2$— and B is indanyl.

In another embodiment A is —(CH$_2$)$_2$S(CH$_2$)$_3$— and B is indanyl.

In another embodiment A is —CH$_2$-Ph-OCH$_2$—, wherein Ph is interphenylene, and B is indanyl.

In another embodiment A is —CH$_2$-mPh-OCH$_2$—, wherein mPh is m-interphenylene, and B is indanyl.

In another embodiment A is —CH$_2$—O—(CH$_2$)$_4$— and B is indanyl.

In another embodiment A is —CH$_2$—O—CH$_2$—Ar—, wherein Ar is 2,5-interthienylene, and B is indanyl.

In another embodiment A is —CH$_2$—O—CH$_2$—Ar—, wherein Ar is 2,5-interfurylene, and B is indanyl.

In another embodiment A is —S(CH$_2$)$_3$S(CH$_2$)$_2$— and B is indanolyl.

In another embodiment A is —(CH$_2$)$_4$OCH$_2$— and B is indanolyl.

In another embodiment A is cis —CH$_2$CH═CH—CH$_2$OCH$_2$— and B is indanolyl.

In another embodiment A is —CH$_2$CH≡CH—CH$_2$OCH$_2$— and B is indanolyl.

In another embodiment A is —(CH$_2$)$_2$S(CH$_2$)$_3$— and B is indanolyl.

In another embodiment A is —CH$_2$-Ph-OCH$_2$—, wherein Ph is interphenylene, and B is indanolyl.

In another embodiment A is —CH$_2$-mPh-OCH$_2$—, wherein mPh is m-interphenylene, and B is indanolyl.

In another embodiment A is —CH$_2$—O—(CH$_2$)$_4$— and B is indanolyl.

In another embodiment A is —CH$_2$—O—CH$_2$—Ar—, wherein Ar is 2,5-interthienylene, and B is indanolyl.

In another embodiment A is —CH$_2$—O—CH$_2$—Ar—, wherein Ar is 2,5-interfurylene, and B is indanolyl.

In another embodiment A is —S(CH$_2$)$_3$S(CH$_2$)$_2$— and B is indanonyl.

In another embodiment A is —(CH$_2$)$_4$OCH$_2$— and B is indanonyl.

In another embodiment A is cis —CH$_2$CH═CH—CH$_2$OCH$_2$— and B is indanonyl.

In another embodiment A is —CH$_2$CH≡CH—CH$_2$OCH$_2$— and B is indanonyl.

In another embodiment A is —(CH$_2$)$_2$S(CH$_2$)$_3$— and B is indanonyl.

In another embodiment A is —CH$_2$-Ph-OCH$_2$—, wherein Ph is interphenylene, and B is indanonyl.

In another embodiment A is —CH$_2$-mPh-OCH$_2$—, wherein mPh is m-interphenylene, and B is indanonyl.

In another embodiment A is —CH$_2$—O—(CH$_2$)$_4$— and B is indanonyl.

In another embodiment A is —CH$_2$—O—CH$_2$—Ar—, wherein Ar is 2,5-interthienylene, and B is indanonyl.

In another embodiment A is —CH$_2$—O—CH$_2$—Ar—, wherein Ar is 2,5-interfurylene, and B is indanonyl.

In another embodiment A is —S(CH$_2$)$_3$S(CH$_2$)$_2$— and B is (1-hydroxycyclobutyl)phenyl.

In another embodiment A is —(CH$_2$)$_4$OCH$_2$— and B is (1-hydroxycyclobutyl)phenyl.

In another embodiment A is cis —CH$_2$CH═CH—CH$_2$OCH$_2$— and B is (1-hydroxycyclobutyl)phenyl.

In another embodiment A is —CH$_2$CH≡CH—CH$_2$OCH$_2$— and B is (1-hydroxycyclobutyl)phenyl.

In another embodiment A is —(CH$_2$)$_2$S(CH$_2$)$_3$— and B is (1-hydroxycyclobutyl)phenyl.

In another embodiment A is —CH$_2$-Ph-OCH$_2$—, wherein Ph is interphenylene, and B is (1-hydroxycyclobutyl)phenyl.

In another embodiment A is —CH$_2$-mPh-OCH$_2$—, wherein mPh is m-interphenylene, and B is (1-hydroxycyclobutyl)phenyl.

In another embodiment A is —CH$_2$—O—(CH$_2$)$_4$— and B is (1-hydroxycyclobutyl)phenyl.

In another embodiment A is —CH$_2$—O—CH$_2$—Ar—, wherein Ar is 2,5-interthienylene, and B is (1-hydroxycyclobutyl)phenyl.

In another embodiment A is —CH$_2$—O—CH$_2$—Ar—, wherein Ar is 2,5-interfurylene, and B is (1-hydroxycyclobutyl)phenyl.

In another embodiment A is —S(CH$_2$)$_3$S(CH$_2$)$_2$— and B is (2-methyl-3-hydroxypropyl)phenyl.

In another embodiment A is —(CH$_2$)$_4$OCH$_2$— and B is (2-methyl-3-hydroxypropyl)phenyl.

In another embodiment A is cis —CH$_2$CH═CH—CH$_2$OCH$_2$— and B is (2-methyl-3-hydroxypropyl)phenyl.

In another embodiment A is —CH$_2$CH≡CH—CH$_2$OCH$_2$— and B is (2-methyl-3-hydroxypropyl)phenyl.

In another embodiment A is —(CH$_2$)$_2$S(CH$_2$)$_3$— and B is (2-methyl-3-hydroxypropyl)phenyl.

In another embodiment A is —CH$_2$-Ph-OCH$_2$—, wherein Ph is interphenylene, and B is (2-methyl-3-hydroxypropyl)phenyl.

In another embodiment A is —CH$_2$-mPh-OCH$_2$—, wherein mPh is m-interphenylene, and B is (2-methyl-3-hydroxypropyl)phenyl.

In another embodiment A is —CH$_2$—O—(CH$_2$)$_4$— and B is (2-methyl-3-hydroxypropyl)phenyl.

In another embodiment A is —CH$_2$—O—CH$_2$—Ar—, wherein Ar is 2,5-interthienylene, and B is (2-methyl-3-hydroxypropyl)phenyl.

In another embodiment A is —CH$_2$—O—CH$_2$—Ar—, wherein Ar is 2,5-interfurylene, and B is (2-methyl-3-hydroxypropyl)phenyl.

In another embodiment A is —S(CH$_2$)$_3$S(CH$_2$)$_2$— and B is (1-hydroxy-2-phenylethyl)phenyl.

In another embodiment A is —(CH$_2$)$_4$OCH$_2$— and B is (1-hydroxy-2-phenylethyl)phenyl.

In another embodiment A is cis —CH$_2$CH═CH—CH$_2$OCH$_2$— and B is (1-hydroxy-2-phenylethyl)phenyl.

In another embodiment A is —CH$_2$CH≡CH—CH$_2$OCH$_2$— and B is (1-hydroxy-2-phenylethyl)phenyl.

In another embodiment A is —(CH$_2$)$_2$S(CH$_2$)$_3$— and B is (1-hydroxy-2-phenylethyl)phenyl.

In another embodiment A is —CH₂-Ph-OCH₂—, wherein Ph is interphenylene, and B is (1-hydroxy-2-phenylethyl)phenyl.

In another embodiment A is —CH₂-mPh-OCH₂—, wherein mPh is m-interphenylene, and B is (1-hydroxy-2-phenylethyl)phenyl.

In another embodiment A is —CH₂—O—(CH₂)₄— and B is (1-hydroxy-2-phenylethyl)phenyl.

In another embodiment A is —CH₂—O—CH₂—Ar—, wherein Ar is 2,5-interthienylene, and B is (1-hydroxy-2-phenylethyl)phenyl.

In another embodiment A is —CH₂—O—CH₂—Ar—, wherein Ar is 2,5-interfurylene, and B is (1-hydroxy-2-phenylethyl)phenyl.

COMPOUND EXAMPLES

Compound Example 1

A compound having the formula

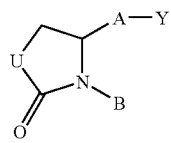

or a pharmaceutically acceptable salt, prodrug, or a metabolite thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

A is —(CH₂)₆—, cis —CH₂CH═CH—(CH₂)₃—, or —CH₂C≡C—(CH₂)₃—, wherein 1 or 2 carbon atoms may be substituted with S or O; or A is —(CH₂)ₘ—Ar—(CH₂)ₒ— wherein Ar is interarylene or heterointerarylene, the sum of m and o is from 1 to 4, and wherein one CH₂ may be substituted with S or O;

U is O, S, NR¹, wherein R¹ is H, C₁₋₆ alkyl, C₁₋₇ acyl, benzoyl, biphenylacyl, C₁₋₆ sulfonyl, phenylsulfonyl, biphenylsulfonyl, trifluoromethylacyl, or trifloyl; and B is aryl or heteroaryl.

Compound Example 2

The compound of compound example 1 wherein B is phenyl.

Compound rimentsExample 3

The compound of compound example 2 wherein B is alkylphenyl.

Compound Example 4

The compound of compound example 2 wherein B is p-t-butylphenyl.

Compound Example 5

The compound of compound example 1 having the formula

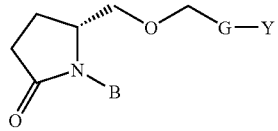

or a pharmaceutically acceptable salt, prodrug, or a metabolite thereof;

wherein G is 1,3-interaryl or interheteroaryl, or —(CH₂)₃—.

Compound Example 6

The compound of compound example 5 wherein B is phenyl.

Compound Example 7

The compound of compound example 6 wherein B is hydroxyalkylphenyl.

Compound Example 8

The compound of compound example 1 having the formula

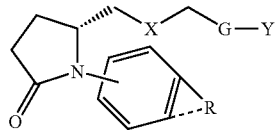

or a pharmaceutically acceptable salt, prodrug, or a metabolite thereof;

wherein a dashed line indicates the presence or absence of a bond;

R is hydrocarbyl or hydroxyhydrocarbyl having from 1 to 12 carbon atoms;

X is CH₂, O, or S; and

G is 1,3-interaryl or interheteroaryl, or —(CH₂)₃—.

Compound Example 9

The compound of compound example 1 having the formula

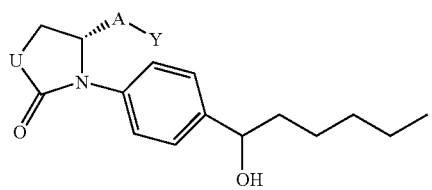

or a pharmaceutically acceptable salt or a prodrug thereof.

Compound Example 10

The compound of compound example 1 having the formula

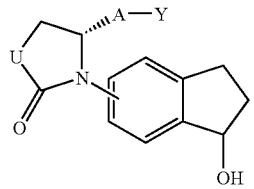

or a pharmaceutically acceptable salt or a prodrug thereof.

Compound Example 11

The compound of compound example 1 having the formula

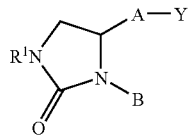

or a pharmaceutically acceptable salt or a prodrug thereof.

Compound Example 12

The compound of compound example 1 having the formula

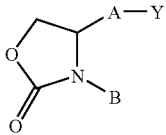

or a pharmaceutically acceptable salt or a prodrug thereof.

Compound Example 13

The compound of compound example 1 having the formula

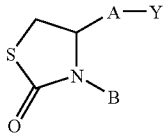

or a pharmaceutically acceptable salt or a prodrug thereof.

Compound Example 14

A compound selected from
(S)-methyl 5-(((3-(4-(1-hydroxyhexyl)phenyl)-2-oxooxazolidin-4-yl)methoxy)methyl)thiophene-2-carboxylate;
(S)-methyl 5-(((3-(4-(1-fluorohexyl)phenyl)-2-oxooxazolidin-4-yl)methoxy)methyl)thiophene-2-carboxylate;
(S)-5-(((3-(4-(1-hydroxyhexyl)phenyl)-2-oxooxazolidin-4-yl)methoxy)methyl)thiophene-2-carboxylic acid; and
(S)-5-(((3-(4-(1-fluorohexyl)phenyl)-2-oxooxazolidin-4-yl)methoxy)methyl)thiophene-2-carboxylic acid.

The compounds of disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension, pulmonary hypertension, or the like, premenstrual tension, urinary calculus, oliguria such as the one caused by acute or chronic failure, hyperphosphaturia, constipation, renal disorders, sexual dysfunction, baldness, cancer, disorder of immune regulation, acute myocardial infarction, vascular thrombosis, ischemic heart disease, congestive heart failure, angina pectoris, and the like. A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

A metabolite is broadly defined as a compound which is formed in vivo from the disclosed compound.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |

-continued

| Ingredient | Amount (% w/v) |
|---|---|
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and α2-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chlorostenol, fluprostenol, 13,14-dihydro-chlorostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids in the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, markets pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

One embodiment is use of a compound in the manufacture of a medicament for the treatment of inflammatory bowel disease, said compound having the formula

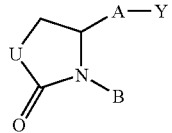

or a pharmaceutically acceptable salt or a prodrug thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O;

U is O, S, $NR^1$, wherein $R^1$ is H, $C_{1-6}$ alkyl, $C_{1-7}$ acyl, benzoyl, biphenylacyl, $C_{1-6}$ sulfonyl, phenylsulfonyl, biphenylsulfonyl, trifluoromethylacyl, or trifloyl; and B is aryl or heteroaryl.

Another embodiment is use of a compound in the manufacture of a medicament for the treatment of inflammatory bowel disease, said compound having the formula

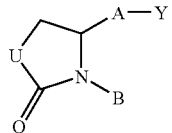

or a pharmaceutically acceptable salt or a prodrug thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O;

U is O, S, $NR^1$, wherein $R^1$ is H, $C_{1-6}$ alkyl, $C_{1-7}$ acyl, benzoyl, biphenylacyl, $C_{1-6}$ sulfonyl, phenylsulfonyl, biphenylsulfonyl, trifluoromethylacyl, or trifloyl; and B is phenyl.

Another embodiment is use of a compound in the manufacture of a medicament for the treatment of inflammatory bowel disease, said compound having the formula

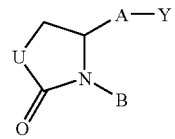

or a pharmaceutically acceptable salt or a prodrug thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O;

U is O, S, $NR^1$, wherein $R^1$ is H, $C_{1-6}$ alkyl, $C_{1-7}$ acyl, benzoyl, biphenylacyl, $C_{1-6}$ sulfonyl, phenylsulfonyl, biphenylsulfonyl, trifluoromethylacyl, or trifloyl; and B is alkylphenyl.

Another embodiment is use of a compound in the manufacture of a medicament for the treatment of inflammatory bowel disease, said compound having the formula

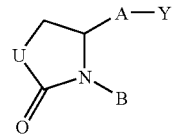

or a pharmaceutically acceptable salt or a prodrug thereof;

wherein

Y is an organic acid functional group, or an amide or ester thereof comprising up to 12 carbon atoms; or Y is hydroxymethyl or an ether thereof comprising up to 12 carbon atoms; or Y is a tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O;

U is O, S, $NR^1$, wherein $R^1$ is H, $C_{1-6}$ alkyl, $C_{1-7}$ acyl, benzoyl, biphenylacyl, $C_{1-6}$ sulfonyl, phenylsulfonyl, biphenylsulfonyl, trifluoromethylacyl, or trifloyl; and B is p-t-butylphenyl.

Another embodiment is use of a compound in the manufacture of a medicament for the treatment of inflammatory bowel disease, said compound comprising

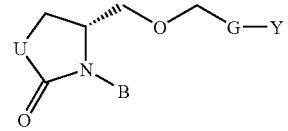

or a pharmaceutically acceptable salt or a prodrug thereof;

wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —(CH$_2$)$_3$—; and
B is aryl or heteroaryl.

Another embodiment is use of a compound in the manufacture of a medicament for the treatment of inflammatory bowel disease, said compound comprising

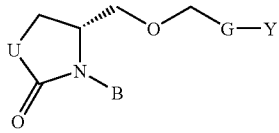

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —(CH$_2$)$_3$—; and
B is phenyl.

Another embodiment is use of a compound in the manufacture of a medicament for the treatment of inflammatory bowel disease, said compound comprising

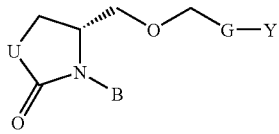

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —(CH$_2$)$_3$—; and
B is hydroxyalkylphenyl.

Another embodiment is use of a compound in the manufacture of a medicament for the treatment of inflammatory bowel disease, said compound having the formula

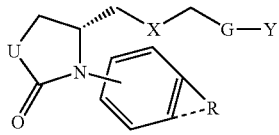

or a pharmaceutically acceptable salt or a prodrug thereof;
wherein a dashed line indicates the presence or absence of a bond;
Y is an organic acid functional group, or an amide or ester thereof comprising up to 12 carbon atoms; or Y is hydroxymethyl or an ether thereof comprising up to 12 carbon atoms; or Y is a tetrazolyl functional group;
R is hydrocarbyl or hydroxyhydrocarbyl having from 1 to 12 carbon atoms;
X is CH$_2$, O, or S; and
G is 1,3-interaryl or interheteroaryl, or —(CH$_2$)$_3$—.

Another embodiment is use of a compound in the manufacture of a medicament for the treatment of inflammatory bowel disease, said compound having the formula

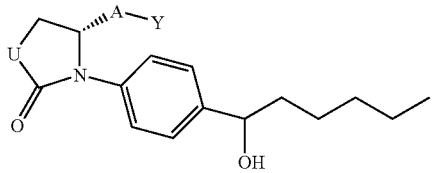

or a pharmaceutically acceptable salt or a prodrug thereof, wherein A, Y, and U are as disclosed herein.

Another embodiment is use of a compound in the manufacture of a medicament for the treatment of inflammatory bowel disease, said compound having the formula

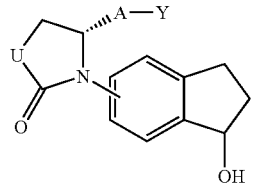

or a pharmaceutically acceptable salt or a prodrug thereof, wherein A, Y, and U are as disclosed herein.

Another embodiment is use of a compound in the manufacture of a medicament for the treatment of inflammatory bowel disease, said compound having the formula

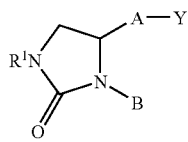

or a pharmaceutically acceptable salt or a prodrug thereof, wherein A, Y, and R$^1$ are as disclosed herein.

Another embodiment is use of a compound in the manufacture of a medicament for the treatment of inflammatory bowel disease, said compound having the formula

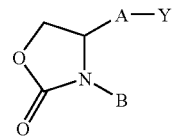

or a pharmaceutically acceptable salt or a prodrug thereof, wherein A and Y are as disclosed herein.

Another embodiment is use of a compound in the manufacture of a medicament for the treatment of inflammatory bowel disease, said compound having the formula

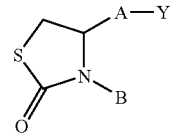

or a pharmaceutically acceptable salt or a prodrug thereof, wherein A and Y are as disclosed herein.

One embodiment is a compound having the formula

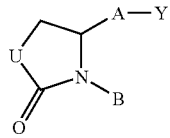

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;
U is O, S, $NR^1$, wherein $R^1$ is H, $C_{1-6}$ alkyl, $C_{1-7}$ acyl, benzoyl, biphenylacyl, $C_{1-6}$ sulfonyl, phenylsulfonyl, biphenylsulfonyl, trifluoromethylacyl, or trifloyl; and
B is aryl or heteroaryl.

Another embodiment is a compound having the formula

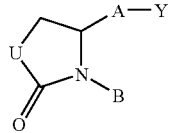

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;
U is O, S, $NR^1$, wherein $R^1$ is H, $C_{1-6}$ alkyl, $C_{1-7}$ acyl, benzoyl, biphenylacyl, $C_{1-6}$ sulfonyl, phenylsulfonyl, biphenylsulfonyl, trifluoromethylacyl, or trifloyl; and
B is phenyl.

Another embodiment is a compound having the formula

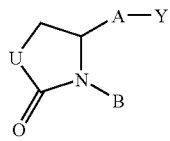

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;
U is O, S, $NR^1$, wherein $R^1$ is H, $C_{1-6}$ alkyl, $C_{1-7}$ acyl, benzoyl, biphenylacyl, $C_{1-6}$ sulfonyl, phenylsulfonyl, biphenylsulfonyl, trifluoromethylacyl, or trifloyl; and
B is alkylphenyl.

Another embodiment is a compound having the formula

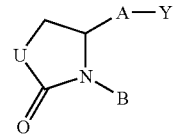

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;
U is O, S, $NR^1$, wherein $R^1$ is H, $C_{1-6}$ alkyl, $C_{1-7}$ acyl, benzoyl, biphenylacyl, $C_{1-6}$ sulfonyl, phenylsulfonyl, biphenylsulfonyl, trifluoromethylacyl, or trifloyl; and
B is p-t-butylphenyl.

Another embodiment is a compound having the formula

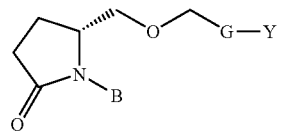

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —$(CH_2)_3$—; and
B is aryl or heteroaryl.

Another embodiment is a compound having the formula

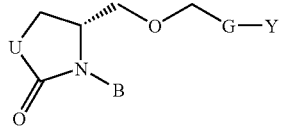

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —(CH$_2$)$_3$—; and
B is phenyl.

Another embodiment is a compound comprising

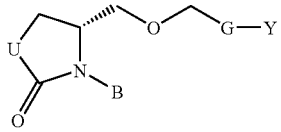

or a pharmaceutically acceptable salt or a prodrug thereof;
wherein
Y is an organic acid functional group, or an amide or ester thereof comprising up to 12 carbon atoms; or Y is hydroxymethyl or an ether thereof comprising up to 12 carbon atoms; or Y is a tetrazolyl functional group;
G is 1,3-interaryl or interheteroaryl, or —(CH$_2$)$_3$—; and
B is hydroxyalkylphenyl.

Another embodiment is a compound having the formula

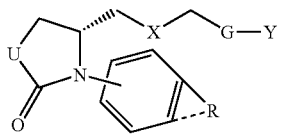

or a pharmaceutically acceptable salt or a prodrug thereof;
wherein a dashed line indicates the presence or absence of a bond;
Y is an organic acid functional group, or an amide or ester thereof comprising up to 12 carbon atoms; or Y is hydroxymethyl or an ether thereof comprising up to 12 carbon atoms; or Y is a tetrazolyl functional group;
R is hydrocarbyl or hydroxyhydrocarbyl having from 1 to 12 carbon atoms;
X is CH$_2$, O, or S; and
G is 1,3-interaryl or interheteroaryl, or —(CH$_2$)$_3$—.

Another embodiment is a compound having the formula

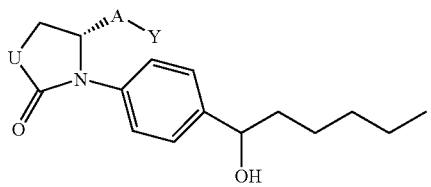

or a pharmaceutically acceptable salt or a prodrug thereof, wherein Y, A, and U are as disclosed herein.

Another embodiment is a compound having the formula

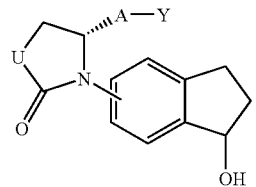

or a pharmaceutically acceptable salt or a prodrug thereof.

Another embodiment is a compound having the formula

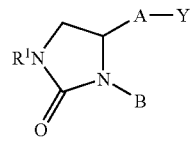

or a pharmaceutically acceptable salt or a prodrug thereof, wherein Y, A, and R$^1$ are as disclosed herein.

Another embodiment is a compound having the formula

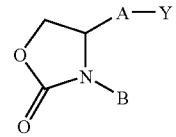

or a pharmaceutically acceptable salt or a prodrug thereof, wherein Y and A are as disclosed herein.

Another embodiment is a compound having the formula

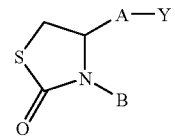

or a pharmaceutically acceptable salt or a prodrug thereof, wherein Y and A are as disclosed herein.

Embodiments contemplated for each compound disclosed herein are use of the compound in the manufacture of a medicament for the treatment of glaucoma or ocular hypertension.

Embodiments contemplated for each compound disclosed herein are use of the compound in the manufacture of a medicament for the treatment of inflammatory bowel disease.

Embodiments contemplated for each compound disclosed herein are methods comprising administering an effective amount of the compound to a mammal for the treatment of glaucoma or ocular hypertension.

Embodiments contemplated for each compound disclosed herein are methods comprising administering an effective amount of the compound to a mammal for the treatment of inflammatory bowel disease.

Embodiments contemplated for each compound disclosed herein are compositions comprising the compound, wherein said compositions are ophthalmically acceptable liquids.

Synthetic Methods

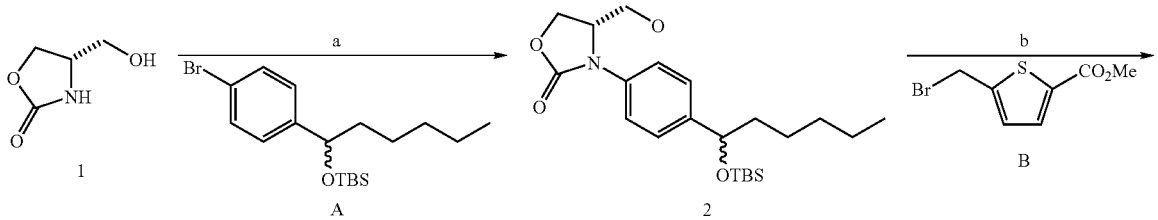

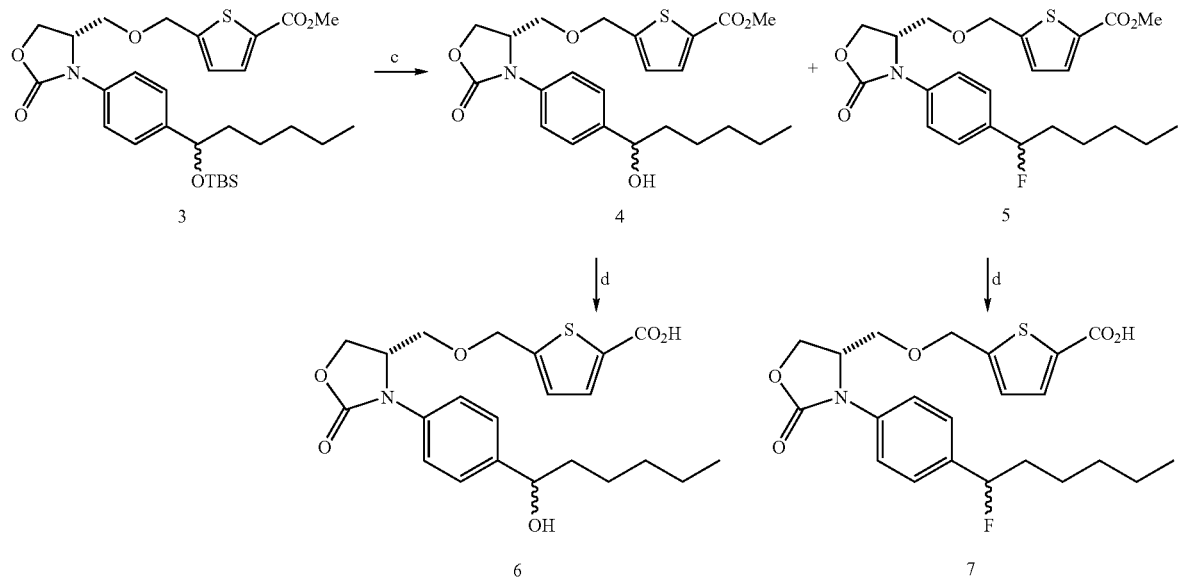

(a) CuI, MeN(H)CH₂CH₂N(H)Me, A, K₂CO₃, MeCN; (b) NaH, B, DMF; (c) HF-pyridine, Mecn; (d) LiOH, H₂O, THF.

EXAMPLE 1

5-{(S)-3-[4-(1-Hydroxy-hexyl)-phenyl]-2-oxo-oxazolidin-4-ylmethoxymethyl}-thiophene-2-carboxylic acid (5)

Step 1. Arylation of 1 to Give 2

Potassium carbonate (730 mg, 5.28 mmol) was added to a solution of (S)-4-hydroxymethyl-oxazolidin-2-one (1, prepared from D-serine methyl ester hydrochloride according to the procedures of Sibi and Renhowe *Tetrahedron Lett.* 1990, 31, 7407-7410, 371 mg, 3.17 mmol) and aryl bromide A (980 mg, 2.64 mmol) (see Provisional Patent Application No. 60/742,779, filed Dec. 6, 2005, which is expressly incorporated by reference herein) in MeCN (6 mL). Copper (I) iodide and N,N'-dimethylethylenediamine were then added and the reaction flask was fitted with a reflux condenser. The reaction mixture was heated at reflux for 3 d, then cooled to room temperature. The mixture was diluted with EtOAc and filtered through celite, washing with excess EtOAc. The filtrate was concentrated in vacuo. Purification of the crude residue by flash column chromatography on 40 g of silica gel (hexane→EtOAc, gradient) afforded 363 mg (34%) of desired alcohol 2.

Step 2. Alkylation of 2 to Give 3

Sodium hydride (60% oil dispersion, 26 mg, 0.65 mmol) was added to a solution of alcohol 2 (180 mg, 0.44 mmol) in DMF (1.1 mL) at 0° C. After 5 min, the reaction was allowed to warm to room temperature. After 30 min at room temperature, the mixture was cooled to a −40° C. and a solution of bromide B (Preparation 1, 125 mg, 0.53 mmol) in DMF (1.1 mL) was added via cannula. After 3 h at −40° C., the reaction was quenched with 1 N HCl (10 mL) and extracted with EtOAc (3×30 mL). The combined extracts were washed with H₂O (2×15 mL) and brine (20 mL), then dried (Na₂SO₄), filtered and concentrated in vacuo. Purification of the crude residue by flash column chromatography on 12 g of silica gel (hexane→EtOAc, gradient) afforded 97 mg (39%) of desired product 3.

Step 3. Deprotection of 3 to Give 4 and 5

HF-pyridine (0.25 mL) was added to a solution of silyl ether 3 (97 mg, 0.17 mmol) in MeCN (3.4 mL) at 0° C. in a plastic scintillation vial. After 1 h at 0° C., the reaction mixture was allowed to warm to room temperature. After 30 min at room temperature, the reaction was quenched with saturated aqueous NaHCO₃ and extracted with EtOAc (3×20 mL). The combined extracts were washed with brine (10 mL), then dried (Na₂SO₄), filtered and concentrated in vacuo. Purification of the crude residue by flash column chromatography on 4 g of silica gel (hexane→EtOAc, gradient) afforded 3 mg (3%) of 3, 6 mg (8%) of fluoride 5 and 62 mg (80%) of alcohol 4.

Step 4. Saponification of 4 to Give 6

Aqueous lithium hydroxide (1 N, 0.3 mL, 0.3 mmol) was added to a solution of ester 4 (26 mg, 0.058 mmol) in THF (0.6 mL). After 18 h at room temperature, the reaction was acidified with 1.0 M HCl (2 mL) then extracted with EtOAc (3×10 mL). Combined extracts were washed with brine (5 mL), dried (Na₂SO₄), filtered and concentrated in vacuo. Purification of the crude residue by flash column chromatography on 4 g of silica gel (CH₂Cl₂→10% MeOH/CH₂Cl₂, gradient) afforded 24 mg (95%) of the title compound (6).

EXAMPLE 2

5-{(S)-3-[4-(1-Fluoro-hexyl)-phenyl]-2-oxo-oxazolidin-4-ylmethoxymethyl}-thiophene-2-carboxylic acid (7)

Aqueous lithium hydroxide (1 N, 0.075 mL, 0.075 mmol) was added to a solution of ester 5 (6 mg, 0.013 mmol) in THF (0.15 mL). After 18 h at room temperature, the solvent was removed under a stream of nitrogen, the residue was acidified with 1.0 M HCl (1 mL) and the mixture was extracted with EtOAc (3×5 mL). Combined extracts were washed with brine (5 mL), dried (Na₂SO₄), filtered and concentrated in vacuo. Purification of the crude residue by flash column chromatography on 4 g of silica gel (CH₂Cl₂→10% MeOH/CH₂Cl₂, gradient) afforded 2.5 mg (43%) of the title compound (7).

Preparation 1

Methyl 5-bromomethyl-thiophene-2-carboxylate (B)

Bromine (0.47 mL, 9.12 mmol) was added to a solution of imidazole (617 mg, 9.06 mmol) and triphenylphosphine (2.40 g, 9.15 mmol) in $CH_2Cl_2$ (30 mL) at room temperature. A solution of methyl 5-hydroxymethyl-thiophene-2-carboxylate (prepared according to the procedures described in WO2004/037808; 1.30 g, 7.59 mmol) in $CH_2Cl_2$ (10 mL) was then added. After 10 min at room temperature, the reaction mixture was concentrated in vacuo. Purification of the crude residue by flash column chromatography on 80 g of silica gel (hexane→EtOAc, gradient) afforded 1.70 g (95%) of the title compound (B).

It is envisioned that a compound such as 2 would serve as a precursor to analogs of compounds 6 and 7 which replace the alpha chain oxygen atom with a carbon atom. This might be accomplished using the procedures in U.S. Provisional Patent Application No. 60/777,506, filed Feb. 28, 2006, which is expressly incorporated by reference herein. Other analogs wherein the alpha chain thiophene is replaced by a different aryl or heteroaryl group are also envisioned.

Furthermore, the analogs of compounds 6 and 7 which replace the core ring oxygen atom with a sulfur atom or a nitrogen atom are also envisioned. Starting material analogs of 1 which might be used to prepare these compounds are (S)-4-hydroxymethylthiazolidin-2-one and (R)-2-oxo-imidazolidine-1,4-dicarboxylic acid 1-benzyl ester 4-methyl ester. (S)-4-Hydroxymethylthiazolidin-2-one would be prepared from D-cysteine according to the procedures described by Han et al., WO2004/019938. (R)-2-Oxo-imidazolidine-1,4-dicarboxylic acid 1-benzyl ester 4-methyl ester would be prepared from (R)—N-Cbz-asparagine (derived from D-asparagine) according to the procedures described by Saijo et al., Chem. Pharm. Bull. 1980, 28, 1459-1467. In the thiazolidinone case, the above procedures described for the oxazolidinone case would apply directly. Other arylation conditions, such as those catalyzed by palladium complexes are also envisioned. Additionally, it may be advantageous to protect the free alcohol of (S)-4-hydroxymethylthiazolidin-2-one prior to the arylation reaction, possibly as its silyl ether. These conditions have been described previously (U.S. Provisional Patent Application No. 60/660,740, filed Mar. 10, 2005, which is now the priority document for PCT Application No. 2006/007797, filed Mar. 6, 2006, both of which are expressly incorporated by reference herein; and U.S. Provisional Patent Application No. 60/777,506, filed Feb. 28, 2006, which is expressly incorporated by reference herein). In the imidazolidinone case, a few additional procedures would be required. Thus, after the arylation of the core ring nitrogen, the methyl ester moiety would be selectively reduced to the hydroxymethyl derivative using $NaBH_4$ in EtOH. After elaboration of the alpha chain, alkaline hydrolysis of the C-1 ester moiety should also remove the Cbz group from the core ring nitrogen atom. Re-esterification of the C-1 acid with diazomethane would then allow selective alkylation or acylation or sulfonylation of the core ring nitrogen atom. Re-hydrolysis (using esterase if necessary for selectivity) would then afford the desired C-1 acid.

Biological Assay Methods

Binding Data

Ki

Competition binding experiments are performed in a medium containing Hank's balanced salt solution, Hepes 20 mM, pH 7.3, membranes (~60 μg protein) or $2×10^5$ cells from HEK 293 cells stably expressing human EP2 receptors, [$^3$H] PGE2 (10 nM) and various concentrations of test compounds in a total volume of 300 μl. Reaction mixtures are incubated at 23° C. for 60 min, and are filtered over Whatman GF/B filters under vacuum. Filters are washed three times with 5 ml ice-cold buffer containing 50 mM Tris/HCl (pH 7.3). Non-specific binding is estimated in the presence of excess unlabeled PGE2 (10 μM). Binding data fitted to the binding model for a single class of binding sites, using nonlinear regression analysis. $IC_{50}$ values thus obtained are converted to Ki using the equation of $Ki=(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors are washed with TME buffer, scraped from the bottom of the flasks, and homogenized for 30 sec using a Brinkman PT 10/35 polytron. TME buffer is added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate is centrifuged at 19000 r.p.m. for 20 min at 4° C. using a Beckman Ti-60 rotor. The resultant pellet is resuspended in TME buffer to give a final 1 mg/ml protein concentration, as determined by Biorad assay. Radioligand binding competition assays vs. [$^3$H-]17-phenyl $PGF_{2\alpha}$ (5 nM) are performed in a 100 μl volume for 60 min. Binding reactions are started by adding plasma membrane fraction. The reaction is terminated by the addition of 4 ml ice-cold TRIS-HCl buffer and rapid filtration through glass fiber GF/B filters using a Brandel cell harvester. The filters are washed 3 times with ice-cold buffer and oven dried for one hour.

[$^3$H-] $PGE_2$ (specific activity 180 Ci mmol) is used as the radioligand for EP receptors. [$^3$H] 17-phenyl $PGF_{2\alpha}$ is employed for FP receptor binding studies. Binding studies employing $EP_1$, $EP_2$, $EP_4$ and FP receptors are performed in duplicate in at least three separate experiments. A 200 μl assay volume is used. Incubations are for 60 min at 25° C. and are terminated by the addition of 4 ml of ice-cold 50 mM TRIS-HCl, followed by rapid filtration through Whatman GF/B filters and three additional 4 ml washes in a cell harvester (Brandel). Competition studies are performed using a final concentration of 5 nM [$^3$H]-$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), are cultured in 100 mm culture dishes in high-glucose DMEM medium containing 10% fetal bovine serum, 2 mM I-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells are seeded at a density of $5×10^4$ cells per well in Biocoat® Poly-D-lysine-coated black-wall, clear-bottom 96-well plates (Becton-Dickinson) and allowed to attach overnight in an incubator at 37° C. Cells are then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates are washed four times with HBSS-HEPES buffer to remove excess dye leaving 100 µl in each well. Plates are re-equilibrated to 37° C. for a few minutes.

Cells are excited with an Argon laser at 488 nm, and emission is measured through a 510-570 nm bandwidth emission filter (FLIPR™, Molecular Devices, Sunnyvale, Calif.). Drug solution is added in a 50 □l volume to each well to give the desired final concentration. The peak increase in fluorescence intensity is recorded for each well. On each plate, four wells each served as negative (HBSS-HEPES buffer) and positive controls (standard agonists: BW245C (hDP); $PGE_2$ (hEP$_1$; hEP$_2$/Gqs5; hEP$_{3A}$/Gqi5; hEP$_4$/Gqs5); $PGF_{2\square}$ (hFP); carbacyclin (hIP); U-46619 (hTP), depending on receptor). The peak fluorescence change in each drug-containing well is then expressed relative to the controls.

Compounds are tested in a high-throughput (HTS) or concentration-response (CoRe) format. In the HTS format, forty-four compounds per plate are examined in duplicates at a concentration of $10^{-5}$ M. To generate concentration-response curves, four compounds per plate are tested in duplicates in a concentration range between $10^{-5}$ and $10^{-11}$ M. The duplicate values are averaged. In either, HTS or CoRe format each compound is tested on at least 3 separate plates using cells from different passages to give an $n \geq 3$.

Results for examples compounds are shown below.

The compounds disclosed useful for the treatment of glaucoma, ocular hypertension, inflammatory bowel disease, and the other diseases or conditions disclosed herein.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:

1. A compound represented by the formula

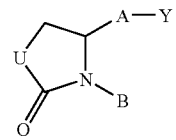

or a pharmaceutically acceptable salt thereof;

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| (structure 1) | 817 | 14 | 2711 | NA | | NA | NA | 995 | NA | NA | >10000 |
| (structure 2) | | 13 | 1043 | | | | | | | | |

Intraocular Pressure (IOP)

Intraocular pressure studies in dogs involve pneumatonometry performed on conscious Beagle dogs of both sexes (10-15 kg). The animals remain conscious throughout the study and are gently restrained by hand. Drugs are administered topically to one eye as a 25 µL volume drop, the other eye receives 25 µL vehicle (0.1% polysorbate 80:10 mM TRIS) as a control. Proparacaine (0.1%) is used for corneal anesthesia during tonometry. Intraocular pressure is determined just before drug administration and at 2, 4 and 6 hr thereafter on each day of the 5 day study. Drug is administered immediately after the first IOP reading.

wherein

Y is an organic acid functional group, or an amide or ester thereof with up to 12 carbon atoms; or Y is hydroxymethyl or an ether thereof with up to 12 carbon atoms; or Y is a tetrazolyl functional group;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

U is O, S, NR$^1$, wherein R$^1$ is H, C$_{1-6}$alkyl, C$_{1-7}$acyl, benzoyl, biphenylacyl, C$_{1-6}$sulfonyl, phenylsulfonyl, biphenylsulfonyl, trifluoromethylacyl, or trifloyl; and B is optionally substituted aryl or optionally substituted heteroaryl.

2. The compound of claim 1 wherein B is phenyl.
3. The compound of claim 2 wherein B is alkylphenyl.
4. The compound of claim 2 wherein B is p-t-butylphenyl.
5. The compound of claim 1 represented by the formula

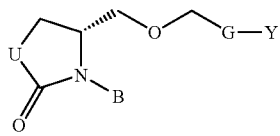

or a pharmaceutically acceptable salt thereof;
wherein G is 1,3-interarylene or interheteroarylene, or —(CH$_2$)$_3$—.

6. The compound of claim 5 wherein B is phenyl.
7. The compound of claim 6 wherein G is interthienylene.
8. The compound of claim 7 wherein B is hydroxyalkylphenyl.
9. The compound of claim 1, represented by the formula

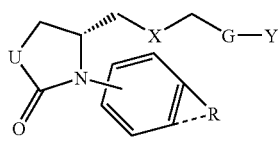

or a pharmaceutically acceptable salt thereof;
wherein a dashed line indicates the presence or absence of a bond;
R is hydrocarbyl or hydroxyhydrocarbyl with from 1 to 12 carbon atoms;
X is CH$_2$, O, or S; and
G is 1,3-interarylene or interheteroarylene, or —(CH$_2$)$_3$—.

10. The compound of claim 9 wherein G is interthienylene.
11. The compound of claim 10 wherein X is CH$_2$.
12. The compound of claim 10 wherein X is O.
13. The compound of claim 1 represented by the formula

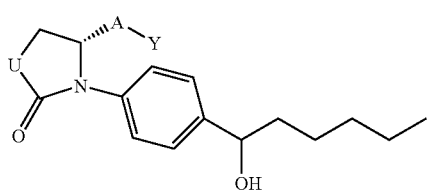

or a pharmaceutically acceptable salt thereof.

14. The compound of claim 1 represented by the formula

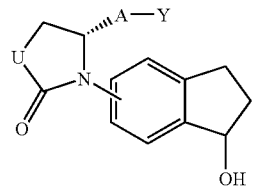

or a pharmaceutically acceptable salt thereof.

15. The compound of claim 1 represented by the formula

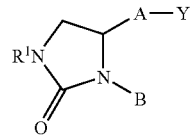

or a pharmaceutically acceptable salt thereof.

16. The compound of claim 1 represented by the formula

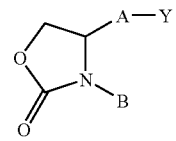

or a pharmaceutically acceptable salt thereof.

17. The compound of claim 1 represented by the formula

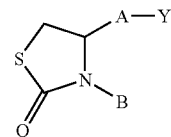

or a pharmaceutically acceptable salt thereof.

18. The compound of claim 1 selected from:
(S)-methyl 5-(((3-(4-(1-hydroxyhexyl)phenyl)-2-oxooxazolidin-4-yl)methoxy)methyl)thiophene-2-carboxylate;
(S)-methyl 5-(((3-(4-(1-fluorohexyl)phenyl)-2-oxooxazolidin-4-yl)methoxy)methyl)thiophene-2-carboxylate;
(S)-5-(((3-(4-(1-hydroxyhexyl)phenyl)-2-oxooxazolidin-4-yl)methoxy)methyl)thiophene-2-carboxylic acid; and
(S)-5-(((3-(4-(1-fluorohexyl)phenyl)-2-oxooxazolidin-4-yl)methoxy)methyl)thiophene-2-carboxylic acid.

19. A method of reducing intraocular pressure comprising administering a therapeutically effective amount of a compound according to claim 1 to an eye of a mammal in need thereof.

20. A composition comprising a therapeutically effective amount of a compound according to claim 1, wherein said composition is ophthalmically acceptable.

* * * * *